(12) United States Patent
Pieczenik

(10) Patent No.: US 6,605,448 B1
(45) Date of Patent: *Aug. 12, 2003

(54) METHOD AND MEANS FOR SORTING AND IDENTIFYING BIOLOGICAL INFORMATION

(76) Inventor: George Pieczenik, 61 W. 62nd St., Apt. 11G, New York, NY (US) 10023

( * ) Notice: Subject to any disclaimer, the term of this patent is extended or adjusted under 35 U.S.C. 154(b) by 140 days.

This patent is subject to a terminal disclaimer.

(21) Appl. No.: 09/193,390

(22) Filed: Nov. 18, 1998

Related U.S. Application Data

(63) Continuation of application No. 07/662,764, filed on Feb. 28, 1991, now Pat. No. 5,866,363, which is a continuation-in-part of application No. 07/201,358, filed on May 26, 1988, now abandoned, which is a continuation of application No. 06/770,390, filed on Aug. 28, 1985, now abandoned.

(51) Int. Cl.$^7$ .......................... C12N 15/64; C12N 15/11; C07K 4/00
(52) U.S. Cl. .................. 435/69.1; 435/69.3; 435/320.1; 530/300; 536/23.1
(58) Field of Search ........................... 435/70.21, 320.1, 435/69.1, 69.3; 530/388.1, 300; 536/23.1

(56) References Cited

U.S. PATENT DOCUMENTS

| | | | |
|---|---|---|---|
| 4,172,124 A | | 10/1979 | Koprowski et al. |
| 4,196,265 A | | 4/1980 | Koprowski et al. |
| 4,237,224 A | | 12/1980 | Cohen et al. |
| 4,359,535 A | | 11/1982 | Pieczenik |
| 4,423,147 A | | 12/1983 | Secher et al. |
| 4,528,266 A | * | 7/1985 | Pieczenik |
| 4,618,578 A | | 10/1986 | Burke et al. |
| 4,625,015 A | | 11/1986 | Green et al. |
| 4,708,871 A | | 11/1987 | Geysen |
| 4,833,092 A | | 5/1989 | Geysen |
| 5,194,392 A | | 3/1993 | Geysen |
| 5,223,409 A | | 6/1993 | Ladner et al. |
| 5,539,084 A | | 7/1996 | Geysen |
| 5,698,426 A | | 12/1997 | Huse |
| 5,723,323 A | | 3/1998 | Kauffman et al. |
| 5,866,363 A | * | 2/1999 | Pieczenik |

FOREIGN PATENT DOCUMENTS

| | | |
|---|---|---|
| DD | A 143794 | 9/1980 |
| DE | 3300 632 A1 | 7/1984 |
| EP | A2 0 048 470 | 3/1982 |
| EP | A1 0 098 118 | 1/1984 |
| EP | A1 0 135 277 | 3/1985 |
| EP | A2 0 154 186 | 9/1985 |
| EP | A2 0 157 643 | 10/1985 |
| GB | 2068971 | 8/1981 |
| GB | 2183661 | 6/1987 |
| WO | 8400687 | 1/1984 |
| WO | WO 84/02922 | 8/1984 |
| WO | WO 84/03506 | 9/1984 |
| WO | WO 84/03564 | 9/1984 |
| WO | WO 85/00807 | 2/1985 |
| WO | WO 85/03725 | 8/1985 |
| WO | WO 86/00991 | 2/1986 |
| WO | WO 86/06487 | 11/1986 |
| WO | 90/15070 | 12/1990 |

OTHER PUBLICATIONS

Benner et al, Regulation of the "Spontaneous" (Background) Immunoglobulin Synthesis, 1981, Int. Archs Allergy appl. Immun. 66: 404–415.*

Mosmann et al, The High Background Immune Reactivity of Mice to Polymorphic Determinants on Xenogeneic Erythrocytes: Theoretical and Practical Implications, Jan. 1982, vol. 128, No. 1, pp. 100–104.*

Abbas, et al, Maturation of B Lymphocytes and Expression of Immunoglobulin Genes, 1981, Cellular and Molecular Immunology, Chapter Four, p. 70.*

Denis et al. Defining the B–Cell Repertoire with Hybridomas derived from Monoclonal Fragment Cultures, Chap. 4, pp. 49–59 in Monoclonal Antibodies Hybridomas: A new dimension in Biological Analyses Kennett et al. Eds. Plenum Press New York, 1980.*

Oliphant et al. Cloning of random–sequence oligodeoxynucleotides Gene vol. 44 pp. 177–183, 1986.*

Horiuchi et al. The filamentous Phage Genome: Genes, Physical Structure, and Protein Products pp. 113–137 in The Single Stranded DNA Phages: Denhardt et al. Eds. Cold Spring Harbor Laboratory, 1978.*

Winger et al. Efficient generation in vitro, from human peripheral blood cells, of monclonal epstein–Barr virus transformants producing specific antibody to a variety of antigens without prior deliberate immunization Proc. Natl. Acad. Sci. USA vol. 80 pa, 1983.*

Reading Theory and Methods for Immunization in Culture and Monoclonal Antibody Production J. Immunol. Meth. vol. 53 pp. 261–291, 1980.*

Alting–Mees et al., Strategies in Molecular Biology 3:1–2, 9 (1990).

Blackwell, T.K. and Weintraub, H. Science 250:1104–1110 (1990).

Cochrane et al., Proc. Natl. Acad. Sci. USA, 79:5651 (1982).

Cwirla et al,. Proc. Natl. Acad. Sci. USA 87:6378–6382 (1990).

Dame, J.B. et al., Science 225:593–599 (1984).

David, Annals of the New York Academy of Sciences 121:404 (1964).

de la Cruz et al., J. Biol. Chem. 263:4318–4322 (1988).

Devlin et al., Science 249:404–406 (1990).

Enea et al., Science 225:628 (1984).

(List continued on next page.)

Primary Examiner—John S. Brusca

(57) ABSTRACT

In one aspect the invention discloses a matrix comprising a discrete population of random oligopeptides of the same length, the length being selected from about 4 to about 12 L-amino acid residues, the population comprising at least 10% of all amino acid sequences of the selected length; and a heterogeneous population of antibodies comprising antibodies capable of binding to substantially every member of the oligopeptide population.

23 Claims, No Drawings

OTHER PUBLICATIONS

Fodor et al., Science 251:767–773 (1991).
Fok et al., Molec. Immunol. 19:1667 (1982).
Geysen et al., Proc. Natl. Acad. Sci. USA 81:3998–4002 (1984).
Geysen et al., Synthetic Peptides as Antigens; Ciba Foundation Symposium 119, R. Porter and J. Wheelan, Eds. (New York, Wiley) pp. 130–149.
Godson et al., Nature 305:29–33 (1983).
Goulian et al., Biochemistry 12(15):2893–2901 (1973).
Huse et al., Science 246:1275–1281 (1989).
Lerner, Nature 299:592 (1982).
Lupski et al., Science 220:1285–1289 (1983).
McCafferty et al., Nature 348: 552–554 (1990).
Mocarski et al., Proc. Natl. Acad. Sci. 82:1266–1270 (1985).
Nunberg et al., Proc. Natl. Acad. Sci. USA 81:3675–3679 (1984).
Orstein, Annals of the New York Academy of Sciences 121:321 (1964).
Parmley and Smith, Gene 73:305–318 (1988).
Robbins et al., J. Mol. Appl. Genet., 2:485–496 (1984), Abstract only.
Scott, J.K. and Smith, G.P. Science 249:386–390 (1990).
Van Eldik et al., Proc. Natl. Acad. Sci. USA 80:6775 (1983).
Van Eldik et al., Arch. Biochem. Biophys. 227:522 (1983).
Wells et al., Gene 34:315–323 (1985).
Winter, G. and Milstein, C., Nature 349:293–299 (1991).
Young et al., Proc. Natl. Acad. Sci. USA 80:1194–1198 (1983).
Smith, Science 228:1315–1317 (1985).

* cited by examiner

SEQUENCE LISTING (1) GENERAL INFORMATION:

(iii) NUMBER OF SEQUENCES: 44

(2) INFORMATION FOR SEQ ID NO: 1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 1:

GATCCTTNNN NNNNNNNNNN NNAA                                            24

(2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

CTTACCGAGC GGACTGGTAA A                                               21

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

CTTATGCAAG ACTCGATACA A                                               21

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CTTGCGGGGT CAGAGGGCGA A                                               21

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

CTTCAGATAT TTCCGAAGCA A                                               21

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

CTTAACATCC TCCAACGGCA A                                               21

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CTTCCATCGC TGAAACTCAA A                                               21

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

CTTACACCGA GGGCGCTCCA A                                               21

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CTTCTAGAAT TCGTGGGCAA A                                               21

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CTTAGCGTGC TCGACAGGCA A                                               21

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

CTTCAAGACA AAGTACATCA A                                                21

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CTTGAAGTAT ATCAAGCAGA A                                                21

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

CTTGTTTTCC TTACTCCCGA A                                                21

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

CTTCTATACA TAACCAACAA A                                                21

(2) INFORMATION FOR SEQ ID NO: 15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CTTGACGCGG ATATAGGAAA A                                                21

(2) INFORMATION FOR SEQ ID NO: 16:

(i) SEQUENCE CHARACTERISTICS:

```
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 41..58

(xi) SEQUENCE DESCRIPTION: SEQ ID NO: 16:

TCTTTACCAG TCCGCTCGGT AAGATCCTCA TGAGGATCTT ACC GAG CGG ACT GGT        55
                                             Thr Glu Arg Thr Gly
                                              1               5

AAA GA                                                                 60
Lys (2) INFORMATION FOR SEQ ID NO: 17:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 17:

Thr Glu Arg Thr Gly Lys
 1               5

(2) INFORMATION FOR SEQ ID NO: 18:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 41..58

(xi) SEQUENCE DESCRIPTION: SEQ ID NO: 18:

TCTTGTATCG AGTCTTGCAT AAGATCCTCA TGAGGATCTT ATG CAA GAC TCG ATA        55
                                             Met Gln Asp Ser Ile
                                              1               5

CAA GA                                                                 60
Gln (2) INFORMATION FOR SEQ ID NO: 19:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 19:

Met Gln Asp Ser Ile Gln
 1               5

(2) INFORMATION FOR SEQ ID NO: 20:

(i) SEQUENCE CHARACTERISTICS:
        (A) LENGTH: 60 base pairs
```

(B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 41..58

(xi) SEQUENCE DESCRIPTION: SEQ ID NO: 20:

TCTTCGCCCT CTGACCCCGC AAGATCCTCA TGAGGATCTT GCG GGG TCA GAG GGC        55
                                                Ala Gly Ser Glu Gly
                                                 1               5

GAA GA                                                                 60
Glu (2) INFORMATION FOR SEQ ID NO: 21:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO: 21:

Ala Gly Ser Glu Gly Glu
 1               5

(2) INFORMATION FOR SEQ ID NO: 22:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 41..58

(xi) SEQUENCE DESCRIPTION: SEQ ID NO: 22:

TCTTGCTTCG GAAATATCTG AAGATCCTCA TGAGGATCTT CAG ATA TTT CCG AAG        55
                                                Gln Ile Phe Pro Lys
                                                 1               5

CAA GA                                                                 60
Gln (2) INFORMATION FOR SEQ ID NO: 23:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO: 23:

Gln Ile Phe Pro Lys Gln
 1               5

(2) INFORMATION FOR SEQ ID NO: 24:

(i) SEQUENCE CHARACTERISTICS:
            (A) LENGTH: 60 base pairs
            (B) TYPE: nucleic acid

```
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 41..58

(xi) SEQUENCE DESCRIPTION: SEQ ID NO: 24:

TCTTGCCGTT GGAGGATGTT AAGATCCTCA TGAGGATCTT AAC ATC CTC CAA CGG        55
                                                 Asn Ile Leu Gln Arg
                                                  1               5

CAA GA                                                                60
Gln (2) INFORMATION FOR SEQ ID NO: 25:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO: 25:

Asn Ile Leu Gln Arg Gln
 1               5

(2) INFORMATION FOR SEQ ID NO: 26:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 41..58

(xi) SEQUENCE DESCRIPTION: SEQ ID NO: 26:

TCTTTGAGTT TCAGCGATGG AAGATCCTCA TGAGGATCTT CCA TCG CTG AAA CTC        55
                                                 Pro Ser Leu Lys Leu
                                                  1               5

AAA GA                                                                60
Lys (2) INFORMATION FOR SEQ ID NO: 27:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO: 27:

Pro Ser Leu Lys Leu Lys
 1               5

(2) INFORMATION FOR SEQ ID NO: 28:

(i) SEQUENCE CHARACTERISTICS:
            (A) LENGTH: 59 base pairs
            (B) TYPE: nucleic acid
            (C) STRANDEDNESS: single
```

(D) TOPOLOGY: linear (ii) MOLECULE TYPE: DNA (genomic)

(ix) FEATURE:
        (A) NAME/KEY: CDS
        (B) LOCATION: 40..57

(xi) SEQUENCE DESCRIPTION: SEQ ID NO: 28:

TCTTGGAGCG CCCTCGGTGT AAGATCCTCT GAGGATCTT ACA CCG AGG GCG CTC         54
                                           Thr Pro Arg Ala Leu
                                             1               5

CAA GA                                                                 59
Gln (2) INFORMATION FOR SEQ ID NO: 29:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 29:

Thr Pro Arg Ala Leu Gln
  1               5

(2) INFORMATION FOR SEQ ID NO: 30:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 41..58

(xi) SEQUENCE DESCRIPTION: SEQ ID NO: 30:

TCTTTGCCCA CGAATTCTAG AAGATCCTCA TGAGGATCTT CTA GAA TTC GTG GGC         55
                                            Leu Glu Phe Val Gly
                                              1               5

AAA GA                                                                  60
Lys (2) INFORMATION FOR SEQ ID NO: 31:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO: 31:

Leu Glu Phe Val Gly Lys
  1               5

(2) INFORMATION FOR SEQ ID NO: 32:

(i) SEQUENCE CHARACTERISTICS:
        (A) LENGTH: 60 base pairs
        (B) TYPE: nucleic acid
        (C) STRANDEDNESS: single
        (D) TOPOLOGY: linear

```
        (ii) MOLECULE TYPE: DNA (genomic)

(ix) FEATURE:
             (A) NAME/KEY: CDS
             (B) LOCATION: 41..58

(xi) SEQUENCE DESCRIPTION: SEQ ID NO: 32:

TCTTGCCTGT CGAGCACGCT AAGATCCTCA TGAGGATCTT AGC GTG CTC GAC AGG       55
                                             Ser Val Leu Asp Arg
                                              1               5

CAA GA                                                                60
Gln (2) INFORMATION FOR SEQ ID NO: 33:

(i) SEQUENCE CHARACTERISTICS:
             (A) LENGTH: 6 amino acids
             (B) TYPE: amino acid
             (D) TOPOLOGY: linear (ii) MOLECULE TYPE: protein (xi) SEQUENCE DESCRIPTION: SEQ ID NO: 33:

Ser Val Leu Asp Arg Gln
 1               5

(2) INFORMATION FOR SEQ ID NO: 34:

(i) SEQUENCE CHARACTERISTICS:
             (A) LENGTH: 60 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 41..58

(xi) SEQUENCE DESCRIPTION: SEQ ID NO: 34:

TCTTGATGTA CTTTGTCTTG AAGATCCTCA TGAGGATCTT CAA GAC AAA GTA CAT       55
                                             Gln Asp Lys Val His
                                              1               5

CAA GA                                                                60
Gln (2) INFORMATION FOR SEQ ID NO: 35:

(i) SEQUENCE CHARACTERISTICS:
             (A) LENGTH: 6 amino acids
             (B) TYPE: amino acid
             (D) TOPOLOGY: linear (ii) MOLECULE TYPE: protein (xi) SEQUENCE DESCRIPTION: SEQ ID NO: 35:

Gln Asp Lys Val His Gln
 1               5

(2) INFORMATION FOR SEQ ID NO: 36:

(i) SEQUENCE CHARACTERISTICS:
             (A) LENGTH: 60 base pairs
             (B) TYPE: nucleic acid
             (C) STRANDEDNESS: single
             (D) TOPOLOGY: linear
```

```
        (ii) MOLECULE TYPE: DNA (genomic)

(ix) FEATURE:
             (A) NAME/KEY: CDS
             (B) LOCATION: 41..58

(xi) SEQUENCE DESCRIPTION: SEQ ID NO: 36:

TCTTCTGCTT GATATACTTC AAGATCCTCA TGAGGATCTT GAA GTA TAT CAA GCA      55
                                             Glu Val Tyr Gln Ala
                                              1               5

GAA GA                                                              60
Glu (2) INFORMATION FOR SEQ ID NO: 37:

(i) SEQUENCE CHARACTERISTICS:
             (A) LENGTH: 6 amino acids
             (B) TYPE: amino acid
             (D) TOPOLOGY: linear (ii) MOLECULE TYPE: protein (xi) SEQUENCE DESCRIPTION: SEQ ID NO: 37:

Glu Val Tyr Gln Ala Glu
 1                   5

(2) INFORMATION FOR SEQ ID NO: 38:

(i) SEQUENCE CHARACTERISTICS:
             (A) LENGTH: 60 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 41..58

(xi) SEQUENCE DESCRIPTION: SEQ ID NO: 38:

TCTTCGGGAG TAAGGAAAAC AAGATCCTCA TGAGGATCTT GTT TTC CTT ACT CCC      55
                                             Val Phe Leu Thr Pro
                                              1               5

GAA GA                                                              60
Glu (2) INFORMATION FOR SEQ ID NO: 39:

(i) SEQUENCE CHARACTERISTICS:
             (A) LENGTH: 6 amino acids
             (B) TYPE: amino acid
             (D) TOPOLOGY: linear (ii) MOLECULE TYPE: protein (xi) SEQUENCE DESCRIPTION: SEQ ID NO: 39:

Val Phe Leu Thr Pro Glu
 1                   5

(2) INFORMATION FOR SEQ ID NO: 40:

(i) SEQUENCE CHARACTERISTICS:
             (A) LENGTH: 60 base pairs
             (B) TYPE: nucleic acid
             (C) STRANDEDNESS: single
             (D) TOPOLOGY: linear (ii) MOLECULE TYPE: DNA (genomic)
```

(ix) FEATURE:
            (A) NAME/KEY: CDS
            (B) LOCATION: 41..58

(xi) SEQUENCE DESCRIPTION: SEQ ID NO: 40:

TCTTTGTTGG TTATGTATAG AAGATCCTCA TGAGGATCTT CTA TAC ATA ACC AAC         55
                                            Leu Tyr Ile Thr Asn
                                             1               5

AAA GA                                                                 60
Lys (2) INFORMATION FOR SEQ ID NO: 41:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO: 41:

Leu Tyr Ile Thr Asn Lys
 1               5

(2) INFORMATION FOR SEQ ID NO: 42:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 41..58

(xi) SEQUENCE DESCRIPTION: SEQ ID NO: 42:

TCTTTTCCTA TATCCGCGTC AAGATCCTCA TGAGGATCTT GAC GCG GAT ATA GGA        55
                                            Asp Ala Asp Ile Gly
                                             1               5

AAG A                                                                  59
Lys (2) INFORMATION FOR SEQ ID NO: 43:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO: 43:

Asp Ala Asp Ile Gly Lys
 1               5

(2) INFORMATION FOR SEQ ID NO: 44:

(i) SEQUENCE CHARACTERISTICS:
            (A) LENGTH: 16 amino acids
            (B) TYPE: amino acid
            (C) STRANDEDNESS: <Unknown>
            (D) TOPOLOGY: linear (ii) MOLECULE TYPE: peptide -continued (xi) SEQUENCE DESCRIPTION: SEQ ID NO: 44:

Asp Asp Glu Val Asp Val Asp Gly Thr Val Glu Glu Asp Leu Gly Tyr
1               5                   10                  15

METHOD AND MEANS FOR SORTING AND IDENTIFYING BIOLOGICAL INFORMATION

This application is a continuation of application Ser. No. 07/662,764, filed Feb. 28, 1991, now U.S. Pat. No. 5,866,363, which is a is a continuation-in-part of U.S. patent application Ser. No. 07/201,358, filed May 26, 1988, now abandoned which hereby incorporated by reference herein, which application is a continuation of U.S. patent application Ser. No. 06/770,390, filed Aug. 28, 1985, now abandoned.

FIELD OF THE INVENTION

This application describes discrete populations of oligopeptides of random sequences, polypeptides comprising those oligopeptides, oligonucleotides encoding those oligopeptides and recombinant vectors comprising those oligonucleotide sequences. The population of oligopeptides represents the universe of peptide epitopes. Also disclosed are discrete populations of antibodies (or hybridomas) capable of binding to the populations of oligopeptides. The disclosure of the present application relates to the identification and characterization of peptide epitopes, or recognition sites, of antibodies. More particularly, the determination of the linear amino acid sequence recognized by the antibody and of a nucleic acid sequence encoding that amino acid sequence are enabled by the disclosure herein.

BACKGROUND OF THE INVENTION

The clonal selection theory of Burnet, which explains the general basis of antibody production, has gained virtually complete acceptance. Burnet, M. (1961) Sci. Am. 204:58; Jerne, N. K. (1976) Harvey Lecture 70:93. The theory is based on several premises: (1) as individual cells, i.e., lymphocytes, in the immune system differentiate, each becomes capable of producing only one species of antibody molecule; (2) the entire spectrum of possible antibody-producing cells is present within the lymphoid tissues prior to stimulation by any antigen; that is, the step in which each lymphocyte becomes specified to produce only one type of antibody molecule occurs in the absence of a potential antigen for that antibody; and (3) lymphocytes capable of producing an antibody specific to a particular antigen are induced, by the presence of that antigen, to proliferate and to produce large quantities of the antibody. An enormous range of genetically unique lymphoid cells is present in the lymphoid organs, e.g., the spleen, of each mammal. The spleen can be considered a library of cells, each of which can manufacture a unique antibody, and the library is so large that for any particular antigen, at least one lymph cell exists within the library that is capable of recognizing the antigen and producing antibodies specific to the antigen.

Heretofore, the production of an antibody that will recognize an antigen of interest has required the antigenic stimulation of a laboratory animal. Typically, the antigen is injected into a laboratory animal, and, after a suitable incubation period, a second injection is given. The spleen cells of the animal are then harvested and fused to myeloma cells. When fused to a spleen cell, the myeloma cell confers to the spleen cell its ability to grow in culture. Surviving colonies of fused cells, i.e., hybridomas, are then screened to identify clones that produce antibodies that specifically recognize the antigen. This procedure must be repeated each time it is desired to produce an antibody to a particular antigen. For each antigen of interest, it is necessary to (1) antigenically stimulate an animal, (2) remove its spleen and hybridize the spleen cells with myeloma cells, and (3) dilute, culture, and screen clones for specific antibody production. Though antibodies that recognize the antigen are produced, this technique does not identify the epitope, i.e., the specific site on the antigen that an antibody recognizes; and one cannot direct the development of antibodies specific to a particular predetermined site or region of the antigen. Also, hybridoma techniques are not effective in the direct development of monoclonal antibodies that recognize haptens, i.e., molecules that contain constitute antibody recognition sites, but which do not elicit an antigenic reaction when injected without a carrier into a laboratory animal. Since antigenic stimulation and antibody production are potentially hazardous to the host, the use of human hosts has been precluded in the development of monoclonal antibodies.

The universe of antibody binding specificities may be open or closed. If the universe of antibody binding specificities is closed, then the following basic tenets apply:

a) one can design and prepare any given epitope and isolate any antibody (for example, a monoclonal antibody produced by a member of a random set of hybridomas) from a universe of antibodies without having first immunized an experimental animal with an antigen containing that epitope. A self-addressing sorting scheme can be used to screen to identify the proper paired correspondence between antibody and epitope;

b) the universe of epitopes can be specified in at least a theoretical fashion, and in principle, can be synthesized; and c) one can independently isolate and identify an antibody-producing hybridoma with the same epitopic specificity as one previously isolated and identified. Such a repeated isolation occurs in a "second hit" experiment, and can be used to estimate the effective size of the universe of antibody specificities. Such an approach is similar in logic to defining a complementation group in genetics.

Even if the universe of epitopes is large, if it is closed, it can be defined by rules, algorithms or iterative analyses.

In the alternative, if the universe of antibody specificities is open, the following principles apply:

a) one cannot isolate an antibody specific for an epitope without prior immunization with an antigen containing that epitope;

b) the universe of epitopes cannot be specified or synthesized; and c) one should not be able to independently isolate more than one antibody with the same target specificity.

The binding domain of a monoclonal antibody specific to a malaria virus surface protein has been identified as being no larger than 40 amino acids long. Cochrane, A. H. et al. Proc. Natl. Acad. Sci. U.S.A. 79:5651 (1982), inserted a 340 base pair sequence from a *Plasmodium knowlesi* gene into the pBR322 vector. The engineered vector produced in *E. coli* a beta-lactamase fusion polypeptide that reacted with a monoclonal antibody specific for a *P. knowlesi* circumsporozoite (CS) protein. This finding indicated that the binding domain of the monoclonal antibody was limited to a region of the CS protein encoded by the inserted sequence, or approximately 110 amino acids. Lupski, J. R. et al., Science 220:1285 (1983), used the same system and, employing transposition mapping techniques, further localized the binding domain to a 40-amino acid region of the CS protein.

Green, N. et al., published PCT application 84/00687, produced antibodies by inoculating laboratory animals with synthetic peptides. Antibodies produced in response to peptides having a length of 8 to 40 amino acid residues and corresponding to sequences in an influenza virus protein were cross-reactive with the virus in vitro.

Dame, J. B. et al., Science 225:593 (1984), sequenced the CS gene of *Plasmodium falciparum* and discovered 41 tandem repeats of a tetrapeptide, with some minor variations. Using synthetic peptides of 4, 7, 11, and 15 amino acid residues of the predominant repeating amino acid sequence, Dame et al. then conducted competitive binding assays to determine what length of peptide would inhibit the binding of the CS protein with a monoclonal antibody specific to that protein. Dame et al. found that the synthetic 4 amino acid sequence did not significantly inhibit binding, but the 7, 11 and 15 amino acid sequences did inhibit binding. These results suggest that this monoclonal antibody to the CS protein recognizes a 5 to 7 amino acid sequence comprising the repeating tetrapeptide.

The known crystal structures of the Fab fragment and lysozyme show that there are two contact points on the lysozyme molecule for the antibody combining site, and each contact point spans over about five amino acids. Earlier work on antibody binding to carbohydrate antigens and glycosidase cleavage protection experiments show that 5–6 sugar residues are protected from glycosidase cleavage. Studies with antibody binding to haptens also suggests that antibody sites are small. Peptide competition experiments, also called epitope mapping experiments, show that oligopeptides 4 to 5 amino acids in length can specifically compete for antibody binding.

In addition, linear sequences which differ in only one amino acid, can compete for antibody binding with varying degrees of specificity (see, e.g., Geysen et al. (1986) in *Synthetic Peptides as Antigens; Ciba Foundation Symposium* 119, R. Porter and J. Wheelan, Eds. (New York, Wiley) pp. 130–149).

While five amino acids is a representative length of peptide sequence which can bind with differential specificity to an antibody, five amino acid residues is not necessarily the size of an immunogenic peptide. Generally, when an oligopeptide is the desired immunogen, it is first conjugated to a larger carrier molecule. The actual operational relationship between the immunizing entity and the binding entity can only be resolved when an in vitro immunization-dependent antibody synthesis system is developed.

SUMMARY OF THE INVENTION

In one aspect the invention features a discrete population of oligonucleotides, each comprising the same length of from about 4 to about 12 nucleic acid coding triplets in random order. Each oligonucleotide encodes a corresponding oligopeptide of from about 4 to about 12 L-amino acid residues, and the entire population represents at least about 10% of all oligopeptide sequences of the selected length. In preferred embodiments, each member of the oligonucleotide population has a single copy of the random sequence of nucleotide triplets, the oligonucleotide sequence has between 4 and 7 triplets, and the oligonucleotide population can be generated by random shearing of mammalian genetic material or is chemically synthesized from the component nucleotides.

It is particularly preferred that each oligonucleotide sequence comprises five coding triplets. The oligonucleotide population may also be composed of members, each of which contains the same number of tandem repeats of each peptide coding sequence, where the number of tandem repeats is from two to about fifty. It is particularly preferred that the oligonucleotide population be sufficiently redundant so that each of all possible encoded oligopeptide sequences is present at least 10 times on average.

In a second aspect the invention features a discrete population of oligopeptides each of random amino acid sequence of the same length, of about 4 to about 12 L-amino acid residues, and the population makes up at least 10% of all peptide sequences of the predetermined length. In preferred embodiments each member of the population has a single copy of the peptide sequence, the oligopeptide sequence has between 4 and 7 L-amino acid residues, and the population can be generated by shearing of proteins, by chemical synthesis from the component L-amino acids, or by the translation of the oligonucleotides of random coding sequences.

It is particularly preferred that there be five amino acid residues in each oligopeptide. It is particularly preferred that the population of oligopeptides is sufficiently large so that each sequence is represented at least 10 times on average. The peptide population can also be composed of member peptides, each of which contains the same number of tandem repeats of the amino acid sequence, where the number of repeats is from two to about fifty.

In a third aspect, the invention features a discrete recombinant vector population of substantially identical autonomously replicating nucleic acid sequences including a structural gene and a population of oligonucleotide inserts therein, each insert containing a uniform length selected from between about 4 to about 12 nucleic acid coding triplets, preferably between 4 and 7, and most preferably five. Each insert is recombinantly inserted in frame into the structural gene of one of the nucleotide sequences, and preferably the oligonucleotide population encodes all oligopeptide sequences of the predetermined length. Preferably the recombinant vector population is redundant, i.e., contains a sufficient number of random oligonucleotide members so that all possible members are represented at least once. It is particularly preferred that the population is sufficiently redundant so that the population contains at least 10 copies of oligonucleotides encoding each possible peptide sequence, on average. In preferred embodiments each member of the insert population has a single copy of the sequence of nucleotide triplets, and the insert has coding triplets; the replicating sequence can be a plasmid such as pBR322, a virus such as λgt11 or vaccinia, or a filamentous bacteriophage, such as f1, fd or M13. The recombinant vector population can also be made up of individual vectors each containing the same number tandem repeats of an oligonucleotide sequence as defined above. The number of tandem repeats can be from two to about fifty in number.

The recombinant vector population can also be made up of individual vectors each containing the same number tandem repeats of an oligonucleotide sequence as defined above the number of tandem repeats can be from two to about fifty in number.

In a fourth aspect, the invention features a discrete heterogeneous population of antibodies comprising member antibodies capable of binding to substantially all members of discrete oligopeptide population featured in the second aspect of the invention, above.

In a fifth aspect, the invention features a discrete population of binding pairs that includes the discrete population of peptide sequences all of the same length selected from about 4 to about 12 L-amino acid residues and the heterogeneous population of antibodies capable of binding to substantially all the peptide sequences, where substantially every member of the peptide population is bound to a corresponding antibody.

In a sixth aspect, the invention features a matrix including a discrete population of random peptide sequences and a heterogeneous population of antibodies.

In a seventh aspect, the invention features a method for constructing a matrix including the steps of (1) obtaining a population of peptides or polypeptides comprising peptides as described above, having a uniform length of between about 4 and about 12 L-amino acid residues of random sequence and including at least about 10% of all peptide sequences of the predetermined length; (2) obtaining a discrete heterogeneous population of antibodies capable of binding to substantially every member of the polypeptide population; and (3) contacting the antibodies with the antigens for a sufficient amount of time and under appropriate conditions so that binding occurs. Preferably, the peptide length is 4 to 7 amino acids, and most preferably, 5 amino acids. In preferred embodiments: each of the peptides and each of the antibodies is isolated and each is contacted individually with each of the antibodies until at least one peptide antibody binding pair is identified; the peptides can be immobilized on an appropriate substrate and the antibodies can be labeled; the antibodies can be immobilized and the peptide sequences can be labeled; or the peptide sequences can be excised from the polypeptides.

It is preferred in all of the foregoing aspects of the invention that the populations be sufficiently large so as to contain all theoretical members of the population, and it is particularly preferred that each population of the invention is sufficiently redundant so that it is statistically unlikely that sampling for a particular member will fail, as is understood in the art.

The invention provides an efficient and convenient means for the identification and production of monoclonal antibodies to any specific region of any antigen or hapten of interest. Monoclonal antibody production, according to the invention, does not require antigenic stimulation of a host animal. This is a critical concept of the present invention. Such antigenic stimulation can be employed to increase the frequency for cognate hybridoma formation, but there will be a member of an antibody population (of a sufficiently large number of members) which will recognize the particular epitope even in the absence of such stimulation.

The invention involves the antibody binding properties of a test species, e.g., a peptide, but is totally independent of the ability of the test species to induce an antigenic response in vivo. The invention permits the identification of the specific peptide sequence on a protein that is recognized by an antibody, i.e., the epitope. The specificity of antibodies recognizing distinct sequences, or epitopes, on the same antigen can be differentiated. In addition, the invention permits the characterization and the localization on a chromosome of the nucleotide sequence encoding the amino acid sequence recognized by an antibody.

Using conventional monoclonal techniques, one can produce antibodies that might react, for example, with an undetermined site on a particular Plasmodium circumsporozooite protein or a particular influenza virus. Using the present invention, one can identify all the epitopes on that molecule or organism and obtain antibodies recognizing each of these epitopes. By judiciously combining a number of distinct antibodies, each of which recognizes a different epitope on the surface of a particular antigen, a material with any desired degree of specificity can be obtained. Also using the invention, one can identify epitopic sequences that are common to, e.g., the circumsporozooite proteins of several Plasmodium species or common to several strains of influenza, and screen for antibodies recognizing these common sequences, thereby identifying a single set of antibodies, each of which is effective against a broad range of malarial or influenza infections.

Certain viruses, such as the LAV or HTLV-III virus, contain on their surfaces both highly mutable regions and constant regions. The viruses' ability to alter their surface characteristics has hampered the development, through standard monoclonal techniques, of antibodies to these viruses. Any antibody that recognizes a mutable region of a virus would become ineffective as the virus mutated to produce strains having altered configurations in the region recognized by the antibody. Once the constant regions of a virus have been identified and characterized, the invention permits the identification and production of antibodies that recognize these constant regions, even if the peptide sequences comprising these constant regions would not themselves elicit an immunogenic response in vivo. Such antibodies would be effective against various mutated strains of the virus.

Other features and advantages of the invention will be apparent from the following description of the preferred embodiments and from the claims.

It is believed that an epitope has limited dimensions of between about 30 and 50 angstroms. An antibody that recognizes a specific peptide sequence or configuration or carbohydrates on the surface of an antigen will recognize that same configuration if it is duplicated or closely approximated on a different antigen. This phenomenon underlies the cross-reactivity sometimes encountered with monoclonal antibodies.

The size of the antibody recognition site corresponds to a peptide sequence in the range of between about 4 and 7 amino acid residues with the majority of recognition sites spanning about 4 to 6 amino acids. Mammalian proteins and polypeptides are composed almost exclusively of the twenty naturally occurring amino acids, i.e., glycine and the L-isomers of alanine, valine, leucine, isoleucine, proline, phenylalanine, tyrosine, tryptophan, serine, threonine, aspartic acid, glutamic acid, asparagine, glutamine, cysteine, methionine, histidine, lysine, and arginine. There are about three million ($20^5$) different possible sequences of the twenty amino acid residues taken five at a time, and about sixty million if the amino acid residues are taken six at a time. This finite number of peptide sequences represents the full range of possible antibody recognition sites which can be represented or mimicked by linear peptide epitopes. Production and maintenance of a representative sample of the full range of antibodies and of a representative sample of the peptide sequences of the appropriate length provides the means (1) to screen any antibody of interest in order to determine the precise epitopic peptide sequence it binds to and (2) to screen any protein in order to find an antibody specific to that protein.

The present invention identifies epitopic (antibody-binding) sites that comprise a primary peptide sequence. The identified linear epitope may mimic a discontinuous peptide epitope or a non-peptide epitope, e.g., a carbohydrate sequence that can be closely approximated by a peptide sequence with respect to antibody recognition.

In view of these considerations, the invention provides the means and methods for the identification and characterization of peptide epitopes, and of the antibodies that bind to them.

DETAILED DESCRIPTION OF THE INVENTION

Antibody Production

According to the clonal selection theory, an unchallenged mammalian host has the capacity to produce antibodies to a vast array of foreign antigens. The presence of an antigen triggers the proliferation of those lymphocytes already present having the ability to produce antibodies specific for that antigen. Since there is a finite number of linear peptide sequences of the length that is recognized by antibodies, it can be expected that each mammal has the capability to produce antibodies that will recognize most, if not all of these sequences. Thus, the spleen of a mouse or another laboratory animal can serve as an appropriate source for a full range of antibodies. The spleen can be harvested from a laboratory animal, and, using standard techniques, the individual cells are fused to myeloma cells and hybridoma strains are developed.

Depending on the desired characteristics of the resulting hybridoma population, either antigenically stimulated animals can be used, or animals that have not been specifically challenged with the antigenic material of interest can be used.

If antigenically stimulated animals are used, then a higher proportion of the resulting hybridomas will produce antibodies specific to the antigen used. If, on the other hand, unchallenged animals are used, then it can be expected that the antibodies retrieved from the resulting population of hybridomas will represent a broader range of the antibodies that the animals are capable of producing. The predominant antibodies produced by a mature animal raised under standard laboratory conditions will reflect and be limited by its individual exposure history. If spleens are harvested from several (at least about 10) unchallenged mature animals and combined together, and the spleen cells fused to myeloma cells, then the resulting discrete population of hybridomas will produce a more complete range of antibodies then would hybridomas from any single individual. Antibodies produced by the hybridomas derived from the spleen cells of mature animals that were raised aseptically or from fetal or neonatal animals that were raised aseptically or from fetal or neonatal animals will not reflect any exposure history and can be expected to represent a random sample of the full range of antibodies that the animals are capable of producing.

Since this procedure does not require antigenic stimulation of donor animals before harvesting the spleens, it is now possible to develop antibodies derived from human cells. Normal spleen cells can be collected from one or a number of human donors and the harvested cells fused to myeloma cells and cultured as described above. Alternatively, a library of human antibodies can be developed over time by obtaining cell cultures from, e.g., a large number of myeloma patients, each patient having a distinctive tumor.

It is now possible to use a recombinant library to generate the universe of antibody binding specificities instead of a hybridoma library. Huse et al. (1989) Science 246:1275–1281, describes the generation of a large combinational library of mouse Fab fragments. Alting-Mees et al. (1990) Strategies in Molecular Biology 3:1–2,9 describes bacteriophage (A) expression libraries for antibody production.

Production of Peptide Sequences

Numerous methods are available for the production of the desired population of peptide sequences. For certain embodiments of the invention these peptide sequences can be produced directly either by randomly shearing proteins and then recovering by electrophoresis the peptide sequences of the appropriate length, or by synthesizing the desired random peptide sequences from the component amino acids.

Alternatively, these peptides can be produced through genetic engineering techniques. Peptides produced according to this general method can be termed coded peptides. A population of nucleotide sequences of the correct length to encode random peptide sequences of the desired length is generated. This can be accomplished either by random cleavage of biological genetic material followed by electrophoresis to recover those nucleotide sequences that were cut or sheared to the desired length, or by chemical synthesis from the component nucleotides or codons.

Depending on the desired characteristics of the resulting population of nucleotide sequences and ultimately, of the peptide sequences to be produced, different techniques are used to obtain the population of nucleotides. If a random population of nucleotide sequences is desired, then the nucleotides can be synthesized by adding the four nucleotides with equal frequency at each position of the growing nucleotide chains. If it is desired that the synthesized nucleotide triplets more closely reflect the distribution of naturally occurring triplets, then the frequency of each nucleotide employed at the first, second, or third position of each triplet can be manipulated to approximate the frequencies at which each nucleotide residue appears at each position in nature, as suggested in Crick F. H. C. et al., Origin of Life, 7:389–397 (1976). Any of several sources of genetic material can be selected to obtain by shearing nucleotide sequences of the desired length, e.g., cellular DNA or cDNA. cDNA, of course, would provide a closer representation of the naturally occurring coding sequences. Alternatively, chemically synthesized oligonucleotides of tandem sequence may be used.

When the desired population of nucleotide sequences has been obtained, the population can then be treated to facilitate the insertion of each sequence into a vector and to facilitate the subsequent recovery of the desired peptide sequence from the culture of host cells incorporating the engineered vector. For example, using known techniques, AUG sequences can be ligated to each end of each member of the population of nucleotide sequences. When each nucleotide sequence is translated, the desired peptide sequence will be flanked by methionine residues. The translated protein can then be treated with cyanogen bromide, which cleaves peptides at methionine sites, to excise the desired peptide sequence from the protein. The cleavage product can then be purified by electrophoresis. Preferably, a restriction endonuclease recognition sequence can be ligated to each end of each member of the population of nucleotide sequences and then the population of nucleotide sequence can be treated with the endonuclease recognizing the ligated sequence to produce "sticky ends" which facilitate the insertion of the nucleotide sequence at the restriction site in a vector recognized by the endonuclease. When the population of nucleotide sequences is chemically synthesized, flanking restriction sites may be designed into the oligonucleotide nucleotide sequence, as understood in the art.

Each nucleotide sequence is then inserted into an appropriate vector. The ratio of nucleotide sequences to vectors can be controlled to ensure that, on the average, no more than one nucleotide sequence is inserted into any vector. The nucleotide sequence must be inserted at a location in the vector where it will be translated in phase when the vector is transferred into an appropriate host cell, and where it will not interfere with the replication of the vector under the experimental conditions employed, i.e., the nucleotide sequence must be inserted into a non-essential region of the vector. Pieczenik, U.S. Pat. Nos. 4,359,535, and 4,528,266 hereby incorporated by reference, disclose a method for inserting foreign DNA into a non-essential region of a vector.

Smith (1985) Science 228:1315–1317 describes the insertion of heterologous coding sequences into the unique BamHI within the minor coat protein (pIII) gene (gene III) of f1 and immunological screening for recombinant phage expressing the heterologous coding sequence. Parmley and Smith (1988) Gene 73:305–318 describe an f1 derivative which allows for the insertion of heterologous coding sequences at an engineered cloning site, allowing for the expression of a heterologous coding sequence near the mature N-terminus of pIII. Immunoaffinity purification can be used to purify recombinant phage expressing a desired epitopic sequence(s).

The nucleotide sequence is advantageously inserted in such a way that the peptide sequence encoded by the nucleotide sequence is expressed on the outside surface of the bacteriophage or the host cells with plasmids containing the nucleotide sequence. To prepare inserts having these characteristics, a vector, e.g., a phage or plasmid, with an appropriate cloning site, is first selected.

A suitable position for a cloning site may be determined empirically by performing an experiment to identify an insertion site in a structural gene which will allow expression of an inserted oligonucleotide coding sequence, and which will result in the expression of the encoded oligopeptide as an epitope within or at one end of a structural gene product such that recognition of the epitope in the recombinant virus or genetically modified host cell or protein is possible. That oligopeptide sequence can be detected using an antibody specific for an epitope of that sequence (or specific for an epitope mimicked by the conformation of that sequence).

The vector can then be cleaved at random sites according to the method disclosed in U.S. Pat. Nos. 4,359,535 and 4,528,266 to yield a population of linear DNA molecules having circularly permuted sequences, where the breakpoint in the circular molecule is at a random location in each molecule. After the cleavage steps, a synthetic oligonucleotide linker bearing a unique nucleotide sequence not present on the original unmodified vector can be attached to both ends of each linearized vector by blunt end ligation. The random linear DNA molecules can then be treated with the restriction endonuclease specific to the attached sequences, to generate cohesive ends.

All such recombinant vectors which allow immunologic detection of the encoded oligopeptide express that epitope in a context-insensitive fashion. For the purposes of this invention, context-insensitive means that the milieu in which the oligopeptide is expressed does not prevent recognition by the cognate antibody. The actual insertion site on the vector can be determined by sequence analysis, as understood in the art, and that site can be modified to contain an appropriate cloning site. As understood in the art, the insertion and immunological detection should be repeated to confirm functionality in context-insensitive expression of an epitopic sequence. Such an engineered vector can be used in the practice of the invention. The immunological detection of an inserted oligonucleotide sequence encoding a context-insensitive epitope is to be called a "topological mapping" of the surface of the vector. The topological mapping of a vector allows the optimum design of an expression vector.

DNA sequences encoding a gene product, e.g., human hemoglobin, where these sequences are not naturally present in the vector, can be cleaved by any method known to the art and fractionated to the desired size, e.g., fifteen nucleotides long, and the nucleotide sequences ligated to the same type of linker used with the random linears. The fractionated nucleotide sequences are then inserted into the random linears, and the modified vectors are transferred into appropriate host cells. The host cells are diluted, plated, and the individual colonies (or plaques) grown up. On replica plates, the colonies (or plaques) are screened with a monoclonal or polyclonal antibody specific to the gene product. A suitable control to insure that selected colonies or plaques express epitopes of the desired specificity is the host cell into which unmodified vector has been introduced, as understood by the skilled artisan.

A positive reaction with the antibody identifies a colony wherein the inserted nucleotide sequence is translated in phase, and the encoded peptide sequence is on the outside surface of the polypeptide or protein, or otherwise accessible to the antibody screening assay. If a monoclonal antibody is employed in the screening step, then this procedure will identify only those colonies where the specific peptide sequence comprising the site recognized by that antibody is inserted on the outside surface of the polypeptide or protein unless appropriate pretreatment has been carried out. If a polyclonal antibody is employed, or a mixture of several monoclonals, then any colony, virus, polypeptide or protein expressing a cognate epitope in a manner accessible for antibody binding will be identified. This procedure identifies recombinant vectors which can be advantageously used in the present invention.

The insertion step creates a discrete population of vectors, each member of the population containing an oligonucleotide insert encoding a different peptide from a population of random amino acid sequences, each encoded peptide sequence containing the same desired number of amino acid residues, preferably five. The discrete population of vectors is then transferred into a population of appropriate host cells. Concentrations of vectors and of host cells can be controlled to ensure that, on the average, no more than one vector is transferred into any individual host cell. Cells are plated and cultured, and the translated proteins are harvested therefrom.

The population of recombinant f1 bacteriophage, as described in Example IV, with random oligonucleotides inserted, will express fusion proteins containing the heterologous peptides of random amino acid sequence. In this embodiment, the heterologous peptides are located within the pIII minor coat protein other insertion sites may be utilized as understood by the skilled artisan for particular desired purposes. For example, Parmley and Smith (1988) Gene 73:305–318 demonstrates the expression of foreign epitopes at the N-terminal end of pIII of f1. Devlin et al. (1990) Science 249:404–406 describes a novel expression vector (M13LP67) derived from M13mp19; foreign epitopes were expressed near the N-terminus of the processed form of B-galactosidase. Cwirla et al. (1990) Proc. Natl. Acad. Sci. USA 87:6378–6382 reports the expression of a population of peptides expressed fused at the N-terminus of pIII of modified bacteriophage fd.

Creating the Matrix

The particular construction of the matrix created from the full range of antibodies or from the peptide sequences described above depends on its use. Either the antibodies or the peptide sequences are immobilized on a solid support substrate or an immobile phase, e.g., nitrocellulose if a two dimensional support is desired or material which can be incorporated in a column if a three dimensional support best serves its purpose, as will be understood by the ordinary skilled artisan. The immobilization can be accomplished by covalently linking the antibodies or peptide sequences to the substrate. Each site on the matrix is occupied by a single chemical species, i.e., a monoclonal antibody or a purified peptide. The source of each individual immobilized species is maintained as a separate culture. In general, the antibodies, the peptide sequences, or the test species are labeled with an appropriate label, such as a fluorescent compound, an enzyme, or a radioactive tracer, as known in the art. The peptide sequence itself can serve as a sensitive biological tag where it occurs on the surface of a protein, virus or modified host cell.

Where the antibodies are immobilized, the peptide sequences or polypeptides comprising those peptide sequences are then contacted with the antibodies under appropriate conditions and for a sufficient amount of time so that each immobilized antibody binds to the peptide sequence to which it is specific. Where the peptide sequences are immobilized, the antibodies are then contacted with the peptide sequences so that each immobilized peptide sequence is recognized and bound by an antibody specific for that particular sequence. Each complex of peptide sequence and its bound antibody can be termed a binding pair. In some cases, the antibodies or peptide sequences themselves are immobilized on the substrate; in other cases the cell cultures producing the antibodies or the modified host cells expressing the peptides are immobilized. Binding pairs are created in a single step, taking advantage of the natural affinity of antibodies for the peptide sequences to which they are specific. If a sample of peptides is contacted with a population of immobilized antibodies, then the peptides will self-sort and each will bind to its corresponding antibody. Similarly, if a sample of antibodies is contacted with a population of immobilized peptides, then the antibodies will self-sort and each will bind to its cognate peptide. The sorting will occur notwithstanding that there is no prior knowledge as to the functional characteristics of any of the individual antibodies or peptides.

A matrix where the antibodies are immobilized on the substrate will be designated an antibody-immobilized matrix, or AIM. Where each immobilized antibody forms a binding pair with a corresponding peptide sequence, the matrix will be designated P-AIM. Similarly, a matrix where the peptide sequences are immobilized matrix, or PIM. Where each immobilized peptide sequence forms a binding pair with a corresponding antibody, the matrix will be designated A-PIM.

Generally, the method of the invention involves contacting a test species with an intact P-AIM or an intact A-PIM, the specific characteristics of the matrix depending on the nature of the information sought as the skilled artisan will readily understand. Considering the large number of different hybridomas, recombinant vectors and genetically modified host cells that are involved in the practice of the invention, the antibodies or peptide sequences can be immobilized very densely on the substrate. Areas of competitive binding are identified when the test species is contacted with the matrix.

Recombinant vectors or modified host cells or colonies from these areas of competitive binding can then be retrieved, repeated less densely, and the competitive binding step with the test species repeated in order to specifically identify the individual colony producing the antibody or amino acid sequence where pairing was disturbed.

Screening an Antibody or Test Species of Interest

A P-AIM is used both to identify and obtain antibody clones that are specific to a test species of interest and to identify the specific peptide sequence recognized by an antibody of interest. The test species can be, for example, a virus, a bacteriophage, a virus coat protein, a surface protein of a viral or bacterial pathogen, a protein on the surface of a malignant cell, an enzyme, or a peptide having the sequence of a selected portion of a protein of interest. The test species need not contain peptides, but may be, e.g., a drug or carbohydrate having a three dimensional structure that is closely approximated by a peptide sequence.

The test species is contacted with a P-AIM in a competitive binding assay with each of the completed binding pairs. Each binding pair occupies a unique site on the matrix. Where these pairs have been labeled, any pairings disturbed by the presence of the test species can be identified.

A particularly sensitive labeling technique is obtained where the peptide sequences bound to the immobilized antibodies are on the surface of a protein or vector. After the P-AIM is created and the binding pairs are established, the P-AIM is thoroughly washed to remove any unbound peptide sequences. The test species is then contacted with the P-AIM. Any peptide sequences that are displaced from their corresponding antibodies by the presence of the test species can be directly titered off the P-AIM. Available techniques are sufficiently sensitive to detect the presence of as few as ten molecules of protein, recombinant vector or modified host cells in the titered supernatant.

Where the test species is labeled, its binding can be detected directly. Each clone producing an antibody that binds to a test species is identified and cultured to provide a source of the antibody. Each culture producing a peptide sequence displaced by the presence of an antibody of interest is identified and cultured to provide a source of that peptide sequence.

A PIM is used both to identify the specific sequences on a test protein or polypeptide that can be recognized by antibodies and to identify the specific peptide sequences recognized by an antibody of interest. Each clone or peptide in a PIM represents the expression or presence of at least $10^4$–$10^7$ copies of the individual peptide sequence so that detection of labeled antibody binding or of the displacement of bound labeled antibody is readily accomplished using techniques known to the art. The procedure for screening on a PIM is analogous to the procedure, above, for screening on an AIM. The test protein or peptide sequence, or the test antibody, is contacted with an intact A-PIM in a competitive binding assay with each of the antibody-peptide sequence pairs. The pairings disturbed by the presence of the test protein or polypeptide or test antibody are noted, and the clones producing the amino acid sequence to which pairing was disturbed are identified and cultured. By this method, not only is it possible to determine the amino acid sequence recognized by the antibody, but it is now possible as well to identify a nucleic acid sequence encoding this amino acid sequence, as the oligonucleotide insert in the vector contained in the clone that produces the recognized amino acid sequence.

EXAMPLE 1

To illustrate certain aspects of the present invention, a method for determining the antibody recognition sites on insulin is described.

Production of Hybridoma Cell Lines

Several C57B1/10 mice are each immunized intraperitoneally with 100 micrograms of human insulin precipitated in alum, mixed with 2×$10^9$ killed *Bordetella pertussis* organisms as adjuvant. A second injection of 100–200 micrograms of insulin in saline is given a month later.

Three days after the second injection, the spleens are removed aseptically and transferred into a sterile bacteriological-type plastic petri dish containing 10 ml of GKN solution. GKN solution contains, per 1 liter of distilled water: 8 g NaCl, 0.4 g KCl, 1.77 g $Na_2HPO_4 \cdot 2H_2O$, 0.69 g NaH$_2$PO$_4$.H$_2$O, 2 g glucose, and 0.01 g phenol red. The cells are teased from the capsule with a spatula. Clumps of cells are further dispersed by pipetting up and down with a 10 ml plastic pipette. The suspension is transferred to a 15 ml polypropylene tube where clumps are allowed to settle for 2 to 3 minutes. The cell suspension is decanted into another tube and centrifuged at 170×G for 15 minutes at room temperature. The cells are washed again in GKN and then resuspended in 1–2 ml GKN. A 20 microliter aliquot of the cell suspension, stained with 1 ml of trypan blue solution, is counted to determine the yield of spleen cells.

$10^8$ washed spleen cells and $5\times10^7$ 8-azaguanine resistant myeloma cells (e.g., cell line X63Ag8.6.5.3; FO; or Sp2/0-Ag14) are combined in a 50 ml conical tube (Falcon 2070). The tube is filled with GKN and centrifuged at 170–200 G at room temperature. The supernatant is withdrawn, and 0.5 ml of a 50% solution of polyethylene glycol in GKN is added dropwise to the pellet. This addition is accomplished over a one minute period at room temperature as the pellet is broken up by agitation. After 90 seconds 5–10 ml of GKN are added slowly over a period of 5 minutes. The cell suspension is then left for 10 minutes, after which large clumps of cells are dispersed by gentle pipetting with a 10 ml pipette. The cell suspension is then diluted into 500 ml of Dulbecco's modified Eagles medium containing 10% fetal calf serum and HAT. 1 ml aliquots are distributed into 480 wells of Costar-Trays (Costar Tissue Culture Cluster 24, Cat. No. 3524, Costar, 205 Broadway, Cambridge, Mass.) each well already containing 1 ml HAT medium and $10^6$ peritoneal cells or $10^6$ spleen cells. The trays are kept in a fully humidified incubator at 37° C. in an atmosphere of 5% CO$_2$ in air. After 3 days and twice a week thereafter, 1 ml medium is removed from each well and replaced with fresh HAT medium. After 7–10 days the wells are inspected for hybrids and the HAT medium is replaced with HT medium. Cell populations of interest are expanded by transfer into cell culture bottles for freezing, cloning, and product analysis. $10^6$ peritoneal cells are added at this time to each culture bottle.

Hybridomas produced by the methods outlined above are propagated and cloned, using standard techniques. The monoclonal antibody produced by each hybridoma line is purified from the culture supernatant and concentrated by affinity chromatography on a protein A-sepharose column.

Production of Gene Library cDNA is synthesized from a heterogeneous population of mRNA, prepared from bovine pancreas. The cDNA is randomly sheared and the 15 nucleotide fragments are retrieved by electrophoresis. These fragments are inserted, in phase, into the structural gene encoding beta-galactosidase of λgt11, according to the methods disclosed in Pieczenik, U.S. Pat. Nos. 4,359,535 and 4,528,266. Cells infected with each of the resulting recombinant bacteriophages produce the normal λgt11 proteins plus a hybrid beta-galactosidase protein containing a foreign sequence of 5 amino acid residues encoded by the 15 nucleotide fragment inserted into the beta-galactosidase (lacz) gene. From 1 microgram of double-stranded oligomeric DNA, 15 base pairs in length, about $6\times10^{10}$ individual sequences can be cloned if cloning is 100% efficient.

Screening and Precise Identification of the Antibody Binding Sites

The library is plated at a density of 25,000 plaques per 150 cm$^2$ plate and immunologically screened, using a pool of those monoclonal antibodies reactive with human insulin and unreactive with unmodified λgt11 phage. The immunological screening is carried out essentially according to the method described by Young et al., Science (1983) 222:778, which is hereby incorporated by reference.

The recombinant λgt11 clones identified by the screening procedure are introduced as lysogens into *E. coli* strain RY 1089 (ATCC 37,196). Lysogens are grown at 32° C. in media containing 50 micrograms of ampicillin per milliliter to an optical density at 550 mm of 0.4 to 0.8. The recombinant phage are induced at 44° C. by shaking gently for 20 minutes and then isopropylthiogalactoside (IPTG) is added to a final concentration of 2 mM, and the culture is shaken an additional hour at 37° C. in order to induce expression of hybrid beta-galactosidase and possible fusion proteins.

Lysates are then analyzed by sodium dodecyl sulfate-polyacrylamide gel electrophoresis (SDS-PAGE) and electroblotted onto nitrocellulose. Pelleted cells from 0.1 ml of each lysogen culture are suspended in 20 microliters of SDS gel sample buffer (3% SDS, 10% glycerol, 10 mM dithiothreitol, 62 MM Tris-HCl, pH 6.8) and proteins are solubilized at 95° C. for 5 minutes before electrophoresis. Proteins are separated by SDS-PAGE according to the method of Laemmli (1970) Nature 277:680 with a 4.5% stacking gel and an 8–12% gradient gel. Western blot analysis is performed according to a modification of the method of Towbin H. et al. (1979) Proc. Natl. Acad. Sci. U.S.A. 79:4350. Each filter is reacted for 90 minutes with a single one of the monoclonal antibodies selected above diluted to a concentration of 1:20,000 with PBS containing 0.05% Tween-20 and 20% FCS. Filter-bound antibody is incubated with [$^{125}$I]-labeled sheep antiserum prepared against whole mouse antibody (diluted to $2\times10^5$ cpm/ml with PBS containing 0.05% Tween-20 and 20% FCS) and then detected by autoradiography. The lysogen that is reactive with the specific antibody used contains the engineered λgt11 clone whose beta-galactosidase enzyme is fused to a 5 amino acid sequence that corresponds to the 5 amino acid sequence of insulin recognized by that antibody. The electrophoresis and electroblotting steps are repeated for each of the monoclonal antibodies selected above, and the specific sequences on the insulin molecule recognized by each of these antibodies are identified by determining the DNA sequences of the oligonucleotide inserts and deducing the respective encoded amino acid sequences.

EXAMPLE II

The method of Example 1 is modified to eliminate the step of inoculating the mice with human insulin. An identical harvesting procedure is used to obtain spleen cells from mice that have not been antigenically stimulated. The spleen cells are hybridized with myeloma cells as described in Example 1, and the resulting hybridomas are propagated and cloned. Notwithstanding the elimination of the antigenic stimulation step, screening identifies clones that produce antibodies reactive with human insulin.

EXAMPLE III

To further illustrate the invention, a method for creating and screening a CDNA expression library will now be described. In this example, the cDNA library is prepared from chicken smooth muscle mRNA.

Production of Gene Library

Total smooth muscle RNA is prepared from 11-day embryonic chicken stomachs and gizzards according to the method of Chirgwin, J. M. et al., (1979) Biochemistry 18:5294 and Feramisco, J. R. et al., (1982) J. Biol. Chem. 257:11024. Poly (A)+ RNA is isolated by two cycles of adsorption to and elution from oligo(dT)-cellulose according to the method of Aviv, H. et al., (1972) Proc. Natl. Acad. Sci. USA 69:1408. Starting with about 25 micrograms of poly(A)+ RNA, first and second strand cDNA is synthesized using avian myeloblastosis virus reverse transcriptase. The double linker method of Kartz and Micodemus, (1981) Gene 13:145 can be employed. The double stranded cDNA, with intact hairpin loops at the ends corresponding to the 5' ends of the poly(A)+ MRNA, are filled in with the Klenow fragment of *E. coli* DNA polymerase I (available, e.g., from Boehringer Mannheim or New England BioLabs). The filled in cDNA is then ligated to [$^{32}$P]-labeled SalI octanucleotide linkers (available from Collaborative Research, Waltham Mass.). The cDNA with SalI linkers attached to the end corresponding to the 3' end of the poly(A)+ mRNA is then treated with nuclease S1 to destroy the hairpin loop and again is filled in with the Klenow fragment of *E. coli* DNA polymerase I. EcoRI octanucleotide linkers (Collaborative Research) are ligated to the cDNA. The DNA is digested to completion with both EcoRI and SalI. A Sepharose 4B column equilibrated with 10 mM Tris-HCl (pH 7.6) containing 1 mM EDTA and 300 mM NaCl is used to isolate and purify those cDNA fragments containing oligonucleotide sequences, 15 nucleotides in length, which are then flanked by the octanucleotide linkers.

The plasmid vector pUC8, described in Vieira et al. (1982) Gene 19:259, is digested to completion with EcoRI and SalI and extracted twice with a 1:1 (v/v) mixture of phenol and chloroform. The 2.9 kilobase fragment is separated from the oligonucleotide fragment on a Sepharose 4B column, equilibrated as set forth above. Fractions containing the large fragment are pooled and precipitated with ethanol. cDNA is ligated to the vector at a weight ratio of vector to cDNA of 1000:1. Approximately 1 nanogram of cDNA is ligated to 1 microgram of the plasmid vector.

Conventional techniques are employed to transform *E. coli* strain DH-1 with the engineered pUC8 vector. The transformed bacterial cells are plated onto 82 mm nitrocellulose filters (Millipore Triton-free HATF) overlaid on ampicillin plates to give about 1,000 colonies per filter. Colonies are replica plated onto nitrocellulose sheets (available from Schleicher & Schuell) and the replicas are regrown both on selective plates for antibody and hybridization screening and on glycerol plates for long-term storage at −70° C.

Antibody Production and Immunological Screening

Each plate is immunologically screened to identify colonies where the plasmid contains a 15 base pair oligonucleotide insert encoding a peptide sequence corresponding to a portion of the chicken tropomyosin gene. Monoclonal antibodies for use in the screening are developed as follows.

Spleen cells are harvested from donor mice that have been antigenically stimulated with chicken tropomyosin. Alternatively, spleen cells can be harvested from mice that have not been antigenically stimulated. The spleen cells are fused to myeloma cells to produce hybridoma strains. The monoclonal antibody produced by each hybridoma line is purified from the culture supernatant and concentrated by affinity chromatography on a protein A sepharose column.

Antibodies are screened for reactivity with chicken tropomyosin and with the parental bacterial strain, DH-1, preferably containing unmodified pUC8. Those antibodies reactive with the tropomyosin and unreactive with DH-1 (pUC8) are selected for use in screening the transformed bacterial colonies.

To prepare the bacterial colonies for screening, cells are lysed by suspending the nitrocellulose filters for fifteen minutes in an atmosphere saturated with $CHCl_3$ vapor. Each filter is then placed in an individual Petri dish in 10 ml of 50 mM Tris-HCl (pH 7.5) 150 mM NaCl, 5 mM $MgCl_2$ containing 3% (wt/vol) bovine serum albumin, 1 microgram of DNase, and 40 micrograms of lysozyme per milliliter. Each filter is agitated gently overnight at room temperature, and then rinsed in saline (50 mM Tris-HCl, (pH 7.5) 150 mM NaCl). Each filter is incubated with a dilute saline solution of a monoclonal antibody selected from those antibodies exhibiting reactivity with tropomyosin but not with DH-1 (pUC8). The filters then are washed five times with saline at room temperature, for one half to one hour per wash. The filters then are incubated with $5 \times 10^6$ cpm of [$^{125}$I]-labeled goat anti-mouse IgG at a specific activity of about $10^7$ cpm/microgram diluted in 10 ml of saline containing 3% bovine serum albumin. The goat anti-mouse IgG can be an affinity purified fraction. The labeling is accomplished according to the chloramine-T procedure of Burridge, K. (1978) Methods Enzymol. 50:57. After one hour of incubation the filters are washed again in saline, with five or six changes, at room temperature, dried, and autoradiographed 24–72 hours, preferably using Dupont Cronex Lightning Plus x-ray enhancing screens. In the immunological screenings, a filter is advantageously included upon which defined amounts of various purified proteins are spotted. This serves as a further control for the specificity of the immunological detection of the antigens. Quantities of less than 1 nanogram of purified protein can be detected in these assays.

This procedure permits the identification and characterization of the specific five amino acid epitopic sequence of the tropomyosin protein that is identified by a particular monoclonal antibody. As this immunological screening process is repeated with different monoclonal antibodies, several distinct antigenic sites on the tropomyosin protein are identified. The 15 nucleotide sequence of cDNA that encodes each antigenic site is preserved in the cDNA-derived library, and a source of antibody that recognizes each site is preserved in the separate hybridoma lines.

Use

The invention is useful to produce antibodies that recognize and bind to particular test species, and to determine either (1) the specific peptide sequence on a protein, enzyme, or peptide that an antibody recognizes or (2) an amino acid sequence with a configuration very close to the structure of a non-peptide or a discontinuous epitopic test species recognized by an antibody. The invention is also useful to determine the nucleotide sequence or sequences according to the codon degeneracy, encoding the amino acid sequence that is recognized by an antibody.

To identify a peptide sequence that closely approximates an antibody binding site on a test species, either an A-PIM or a P-AIM can be used. If an A-PIM is used, then the test species is first contacted with the intact A-PIM. Any antibodies bound to immobilized peptide sequences that have an affinity for the test species will be "competed off" the matrix to bind to the test species. The peptide sequence immobilized at a site where antibodies are "competed off" has a conformational similarity to the site on the test species where the antibodies are now bound. If a P-AIM is used, then the test species is first contacted with the intact P-AIM. The test species displaces any peptide sequences that have a sufficient conformational similarity to an antibody recognition site on the test species that an antibody capable of binding to the peptide sequence is also capable of binding to the test species. Displaced peptide sequences can then be titered off the matrix and identified. It is not necessary that the test species be proteinaceous or derived from peptides.

It can be, for example, a carbohydrate or a non-peptide drug. It can be expected that the recognition site of a non-peptide substance can be closely approximated by the conformation of a peptide sequence or that a linear amino acid sequence can mimic a discontinuous epitope. A test species can disturb the binding at more than a single site on a matrix; this could occur because there is more than one distinct antibody recognition site on the test species or because two ore more distinct peptide sequences are each similar in conformation to a single epitope on the test species. It is not necessary that the test species be immunogenic, i.e., induce the production of antibodies in vivo if inoculated into a mammal; the antibody binding sites of a test species can be characterized even when that test species is not immunogenic.

Where the test species is a disease producing agent, such as a virus or a bacterium, then the peptide sequences that are similar in conformation to the antibody recognition sites of the disease producing agent can be employed to develop a vaccine. A synthetic antigen incorporating the identified peptide sequence or sequences, when injected into a patient's bloodstream, can induce the production of antibodies against the disease producing agent.

Where the test species is the recombinant gene product 1s of a gene expression library, one can determine precisely what regions of the gene product make up antibody recognition sites. The identified peptide sequences correspond to sequences contained in the gene product that are recognized by antibodies.

Where the test species is a gene product, such as, for example, a protein, an enzyme, or a peptide, then the invention also provides a means for locating in a genome the gene encoding that gene product. After the peptide sequences identified from screening the gene product through the matrix are identified, the recombinant cell lines that produced those peptide sequences are identified and the oligonucleotide sequences encoding those peptide sequences are determined. The nucleotide sequences can then be used as DNA probes to locate on the genome the gene encoding for the gene product. Since each nucleotide sequence is fairly short, i.e., from about 5 to about 12 triplets in length, it can be expected that any one sequence, or a closely similar sequence, would be repeated more than once in the genome. Therefore, several distinct nucleotide sequences, each encoding a distinct peptide sequence, are advantageously employed in DNA probes. A region on a chromosome where several nucleotide sequences hybridize in close proximity identifies the DNA fragment containing the gene encoding for the gene product.

To determine the peptide sequence recognized by a particular antibody of interest, either a PIM or a P-AIM can be used. If a PIM is used, it is not necessary that each immobilized peptide sequence be bound to a corresponding antibody. The antibody of interest can be contacted directly with a matrix of immobilized peptide sequences. Any immobilized sequences that are bound by the antibody of interest can then be directly identified. If a P-AIM is used, then the antibody of interest is first contacted with the intact P-AIM. Any peptide sequences bound to immobilized antibodies that can be recognized by the antibody of interest will be "competed off" the matrix to bind with the antibody of interest. Peptide sequences that have been "competed off" the matrix by the presence of the antibody of interest can then be titered off the matrix and identified.

Where it is desired to determine the nucleotide sequence encoding the peptide sequence recognized by an antibody of interest, the modified host cell or recombinant protein or virus that produces the peptide sequence recognized by the antibody can be identified and the nucleotide sequence encoding the peptide sequence can be recovered and the sequence can be determined.

Where the antibody of interest is an anti body produced by a patient suffering from an autoimmune disease and the antibody attacks the patient's own cells or protein, impairing the functioning of those cells or protein, then the peptide sequence recognized by the antibody can provide a basis for treating the patient. The peptide sequence recognized by the antibody can be administered to the patient in an amount effective for competitively inhibiting the antibody from attacking the patient's own cells or protein in vivo. The patient's condition will be improved since fewer antibodies will be available to attack the living cells or functional protein. The administration of peptides will not induce further antibody production since the peptides are too short to induce an immunogenic response.

To identify an antibody that reacts with a test species, an AIM is used. It is not necessary that each immobilized antibody be bound to a corresponding peptide sequence. The test species can be contacted directly with a matrix of immobilized antibodies. Any immobilized antibodies bound to the test species can be directly identified, and the clones producing those antibodies can be cultured to provide a source of the antibodies. It is not necessary that the test species be proteinaceous or derived from peptides. It can be, for example, a carbohydrate or a non-peptide drug. It is not necessary that the test species be immunogenic. It is possible to obtain antibodies that recognize a test species even though the test species, itself, does not induce antibody production in vivo.

The antibodies that recognize the test species can be used in an immunoassay to test for the presence of the test species in a biological sample.

Where the test species is associated with a disease, then an antibody (or antibodies) that recognizes the test species can be used in a diagnostic test kit to determine the condition of a patient. The antibody(ies) is contacted with an appropriate sample from the patient to test for the presence of the test species, which is associated with a particular disease. The antibody(ies) can be incorporated into a diagnostic test kit that recognizes one or more epitopes on a disease-associated substance.

Where the test species is a population of malignant cells from a patient, e.g., cancer cells, then an antibody that specifically recognizes the malignant cells while not recognizing healthy cells from the patient can be used to target drugs to the malignant cells. A sample of malignant cells is contacted with an AIM and antibodies that bind to the malignant cells are identified. A sample of healthy cells from the patient is contacted with a replica of the matrix, and antibodies that bind to the malignant cells, but not to the healthy cells, are selected. A hybridoma line producing selected antibodies is cultured to provide a source of the selected antibodies. A drug, or other cytotoxic agent, is then linked to the selected antibodies, and a therapeutically effective amount of the drug-linked antibodies is administered to the patient.

EXAMPLE IV

This example demonstrates the incorporation of a discrete population of oligonucleotides encoding a population of peptides, each peptide comprising five amino acids in random order, into the f1 gene encoding the minor coat protein pIII (gene III). Thus, a discrete population of recombinant vectors was produced.

The universe of peptides of random sequence, each five amino acids in length, is $5^{20}$, or $3.2 \times 10^6$.

One way to generate each pentapeptide sequence is to take advantage of the fact that a population of random nucleotide sequences, each 15 nucleotides in length, can encode the population of random peptide sequences each five amino acids in length.

Because the genetic code is degenerate, i.e., there are 61 codons coding for 20 amino acids; each amino acid, on the average, has 61/20 or 3.05 synonymous codons. In terms of the nucleotide universe, there are 61 to the power 5 possible nucleotide sequences coding for the 3.2 million pentameric epitopes. Therefore, there are 844,596,301 possible nucleotide sequences coding for 3,200,000 possible pentapeptide sequences. This means that there are 263.94 synonymous codings for each pentapeptide sequence. This high degree of synonymous degeneracy allows us one way of evaluating whether one has generated the universe of possible pentameric epitopes. Generating 3–5 synonymous representations of the coding for the pentapeptide universe statistically suggests an almost complete representation of each member of the pentameric universe. That is, if the nucleotide distribution generated is equimolar and random, one would expect that if one randomly generated 3–5 synonymous codings for any particular pentameric peptide sequence, one would have had a statistically good chance of having generated any other pentameric peptide sequence in the population of 3.2 million possible pentamers.

A discrete population comprising a random distribution of nucleotide sequences (15 mers) and thereby at least one copy of each of the sequences encoding all possible pentapeptides was chemically synthesized as oligonucleotides of the formula GATCCTTN$_{15}$AA SEQ ID NO:2 where N is G, A, T or C. The 15 base random sequences are the coding sequences for the peptide epitope universe. $4^{16}$ or 4, 294, 967, 296 different molecules were synthesized at an average of 243 codings per pentapeptide sequence, this represents a population with about five-fold redundancy. About 1 microgram of DNA was recovered and 108–109 recombinant phage were produced. The TT and AA bases at the 5' and 3' ends, respectively, will allow the sequence to base pair with itself in phase on both strands if GAT is in the sense phase. In addition, the oligonucleotide, after hybridizing to a complementary oligonucleotide, can be ligated in a BamHI site without regenerating a BamHI site so that a BamHI selection against parental molecules lacking inserts can be performed.

One test of the randomness of the chemical synthesis is that half of the approximately $4.2 \times 10^9$ oligonucleotides should be able to form duplexes with the other half. The oligonucleotides were purified on a Sep Pak™ (Millipore, Waters Chromatography, Milford, Mass.) column, lyophilized and resuspended in ligation buffer, heated at 100° C. 5 min and brought to room temperature slowly and incubated overnight. The duplexed oligonucleotides were then ligated into f1 RF DNA which had been previously digested with BamHI and purified after a garose gel electrophoresis. The ligation mixture was transfected after BamHI digestion into freshly prepared competent E. coli TGI cells and plated essentially as described (Smith (1985) Science 228:1315–1317). E. coli TGI is a RecA derivative of E. coli JM101.

Representative plaques were picked and screening using only one sequencing track to identify bacteriophage with inserts. About one-third of the plaques screened were derived from bacteriophage-carrying inserts. These recombinant bacteriophage were plaque-purified and the inserts were sequenced essentially as described in de la Cruz et al. (1988) J. Biol. Chem. 263:4318–4322. Table 1 shows the oligonucleotide sequences of fourteen randomly chosen inserts. The accompanying statistical analysis shows that the observed base distribution is not significantly different from the expected random (equimolar) distribution of bases. Thus, it was confirmed that random oligonucleotides could be synthesized, a particular oligonucleotide could find its complement (or one sufficiently similar to allow duplexing) and that a sequence inserted in an f1 vector was stable. Furthermore, the recombinant bacteriophages were viable.

Several of the amino acid sequences encoded by the fourteen random oligonucleotides of Table 2 are also found in databases of protein sequences (Genbank, *Atlas of Protein Structure and Sequence*) at a frequency expected for a codon distribution determined by random nucleotide sequences. The fourteen translated sequences and the proteins containing identical amino acid sequences are given in Table 2.

TABLE 1

Base Composition Analysis of Randomly Synthesized Coding for Epitopes

| | | |
|---|---|---|
| 1) | CTT ACCGAGCGGACTGGT AAA | SEQ ID NO:2 |
| 2) | CTT ATGCAAGACTCGATA CAA | SEQ ID NO:3 |
| 3) | CTT GCGGGGTCAGAGGGC GAA | SEQ ID NO:4 |
| 4) | CTT CAGATATTTCCGAAG CAA | SEQ ID NO:5 |
| 5) | CTT AACATCCTCCAACGG CAA | SEQ ID NO:6 |
| 6) | CTT CCATCGCTGAAACTC AAA | SEQ ID NO:7 |
| 7) | CTT ACACCGAGGGCGCTC CAA | SEQ ID NO:8 |
| 8) | CTT CTAGAATTCGTGGGC AAA | SEQ ID NO:9 |
| 9) | CTT AGCGTGCTCGACAGG CAA | SEQ ID NO:10 |
| 10) | CTT CAAGACAAAGTACAT CAA | SEQ ID NO:11 |
| 11) | CTT GAAGTATATCAAGCA GAA | SEQ ID NO:12 |
| 12) | CTT GTTTTCCTTACTCCC GAA | SEQ ID NO:13 |
| 13) | CTT CTATACATAACCAAC AAA | SEQ ID NO:14 |
| 14) | CTT GACGCGGATATAGGA AAA | SEQ ID NO:15 |
| T) | 0 4 1 3 5 0 4 7 4 1 3 2 0 3 2 0 = 39 | |
| C) | 5 4 4 2 3 4 5 1 4 3 6 2 5 2 6 6 = 50 | |
| G) | 4 1 3 7 1 6 2 2 3 5 0 5 5 6 3 3 = 53 | |
| A) | 5 5 6 2 5 4 3 4 3 5 5 5 4 3 3 5 = 62 | |
| Totals 14 × 15 = 210 | | 210 |

| Coding Strand Composition | Phage Strand(+) Composition |
|---|---|
| T=39/210=18.6% | = A |
| C=56/210=26.7% | = G |
| G=53/210=25.2% | = C |
| A=62/210=29.5% | = T |
| T 25−18.6 =  6.4 ×  6.4 = 40.96/25 = 1.64 | |
| C 25−26.7 = −1.7 ×  1.7 =  2.09/25 =  .18 | |
| G 25−25.2 = −0.2 × −0.2 =   .04/25 =  .04 | |
| A 25−29.5 = −4.5 × −4.5 = 20.25/25 =  .81 | |
| $X^2$ | 2.57; 3D.F |

A distribution with a Chi-square of 2.57 and 3 degrees of freedom can be gotten randomly 50% of the time.

Therefore, our observed distribution does not differ significantly from our expected (and synthesized) global base composition.

TABLE 2

```
 1) TCTTTACCAGTCCGCTCGGTAAGATCCTCA
    TGAGGATCTTACCGAGCGGACTGGTAAAGA            SEQ ID NO:16
            THRGLUARGTHRGLYLYS
              T   E   R   T   G   K          SEQ ID NO:17
    Phaseolin-Kidney bean
 2) TCTTGTATCGAGTCTTGCATAAGATCCTCA
    TGAGGATCTTATGCAAGACTCGATACAAGA            SEQ ID NO:18
              M   Q   D   S   I   Q          SEQ ID NO:19
 3) TCTTCGCCCTCTGACCCCGCAAGATCCTCA
    TGAGGATCTTGCGGGGTCAGAGGGCGAAGA            SEQ ID NO:20
              A   G   S   F   G   E          SEQ ID NO:21
 4) TCTTGCTTCGGAAATATCTGAAGATCCTCA
    TGAGGATCTTCAGATATTTCCGAAGCAAGA            SEQ ID NO:22
              Q   I F   P   K   Q            SEQ ID NO:23
 5) TCTTGCCGTTGGAGGATGTTAAGATCCTCA
    TGAGGATCTTAACATCCTCCAACGGCAAGA            SEQ ID NO:24
              N   I   L   Q   R   Q          SEQ ID NO:25
    Fibrinogen gamma B chain precursor
    Fibrinogen gamma A chain precursor
 6) TCTTTGAGTTTCAGCGATGGAAGATCCTCA
    TGAGGATCTTCCATCGCTGAAACTCAAAGA            SEQ ID NO:26
              P   S   L   K   L   K          SEQ ID NO:27
    P3 protein-Bluetongue virus
    H-2 class 1-related secreted histocompatability
 7) TCTTGGAGCGCCCTCGGTGTAAGATCCTC
    TGAGGATCTTACACCGAGGGCGCTCCAAGA            SEQ ID NO:28
              T   P   R   A   L   Q          SEQ ID NO:29
    RNA-directed RNA polymerose
 8) TCTTTGCCCACGAATTCTAGAAGATCCTCA
    TGAGGATCTTCTAGAATTCGTGGGCAAAGA            SEQ ID NO:30
              L   E   F   V   G   K          SEQ ID NO:31
 9) TCTTGCCTGTCGAGCACGCTAAGATCCTCA
    TGAGGATCTTAGCGTGCTCGACAGGCAAGA
              SERVALLEUASPARGGLN              SEQ ID NO:32
              S   V   L   D   R   Q          SEQ ID NO:33
    Coat protein-Cauliflower mosaic virus
    Anthranilate synthase
10) TCTTGATGTACTTTGTCTTGAAGATCCTCA
    TGAGGATCTTCAAGACAAAGTACATCAAGA            SEQ ID NO:34
              Q   D   K   V   H   Q          SEQ ID NO:35
    Beta casein-bovine
11) TCTTCTGCTTGATATACTTCAAGATCCTCA
    TGAGGATCTTGAAGTATATCAAGCAGAAGA            SEQ ID NO:36
              E   V   Y   Q   A   E          SEQ ID NO:37
    Nucleoapsid protein N-Punta Toro phlebovirus
    Tyrosine amino transferase-rat
12) TCTTCGGGAGTAAGGAAAACAAGATCCTCA
    TGAGGATCTTGTTTTCCTTACTCCCGAAGA            SEQ ID NO:38
              V   F   L   I   P   E          SEQ ID NO:39
    Pol polyprotein-Bovine leukemia virus
13) TCTTTGTTGGTTATGTATAGAAGATCCTCA
    TGAGGATCTTCTATACATAACCAACAAAGA            SEQ ID NO:40
              L   Y   I   T   N   K          SEQ ID NO:41
14) TCTTTTCCTATATCCGCGTCAAGATCCTCA
    TGAGGATCTTGACGCGGATATAGGAAAGA             SEQ ID NO:42
              D   A   D   I   G   K          SEQ ID NO:43
```

EXAMPLE V

Rabbit polyclonal antibodies specific for the N-terminus of endoplasmin were prepared as described herein.

A peptide containing the N-terminal fifteen amino acid residues of endoplasmin, with an added C-terminal tyrosine residue, is synthesized as described (Cameron et al. (1987) J. Chem. Soc. Chem. Commun. 0(4):270–272). The sequence synthesized is Asp-Asp-Glu-Val-Asp-Val-Asp-Gly-Thr-Val-Glu-Asp-Leu-Gly-Tyr.

The synthetic peptide was coupled, in separate reactions, to keyhole limpet hemocyanin (KLH) and bovine serum albumin (BSA) in a ratio of 5mg peptide to 30mg carrier protein (KLH or BSA), using bis-diazotized o-tolidine. The peptide was suspended at a concentration of 5 mg/ml in 0.16M sodium borate, 0.9% NaCl (pH 9.0). The protein was suspended at 30 mg/ml in the same buffer. The o-tolidine was diazotized by dissolving 0.23 g o-tolidine HCl in 45 ml 0.2M HCl, and adding 0.75 g sodium nitrate in 5 ml water. The mixture was stirred at 4° C. for 60 min, aliquots were then stored at −20° C.

To conjugate peptide to carrier protein, 5 mg peptide, 15 mg protein and 0.6 ml bis-diazotized o-tolidine were mixed, the volume was adjusted to 4 ml and the pH was adjusted to 7.4. The reaction was carried out in the dark at 4° C. for 2 hr. Excess reagents were removed by dialysis at the 4° C. (against 5 l water for 4 h; against 5 l PBS overnight). Peptide conjugates were stored in 50% glycerol in PBS (vol/vol) at −20° C.

Rabbit antisera were produced by injecting 5 mg peptide-protein conjugate in 2 ml 50% Freunds adjuvant every 14 days until an antibody response was detected using standard techniques.

Antibody specific for the peptide-protein conjugate was affinity purified from immune sera using a KLH-peptide strip prepared as described in Smith et al. (1984) J. Cell Biol. 99:20–28.

Defining the Endorplasmin Epitope

Peptides were chemically synthesized, each of which was a contiguous five amino acid sequence from the N-terminal amino acid sequence of endoplasmin. These peptides were immobilized to a solid support in individual spots. Polyclonal antibodies (as described above) were allowed to bind to the immobilized peptides. Detection of the bound antibody revealed that only the peptide comprising amino acids 2–6 of endoplasmin bound antibody molecules.

Recombinant phage with the chemically synthesized 15 bp oligonucleotide encoding the known epitope (amino acids 2–6) of endoplasmin with BamHI-compatible ends are prepared by inserting the coding sequence into BamHI-cut f1 RF.

Recombinant phage are propagated in liquid culture and partially purified from cell-free supernatants by three cycles of polyethylene glycol-salt precipitation and resuspension. The final supernatant is spun at high speed (about 100,000× G) to pellet the phage. The gelatinous phage pellet (containing about 1011–1012 phage) is resuspended in about 50 microliters 0.2% Ponceau S in 6% acetic acid. Glycerol and tracking dye are added to make the sample sufficiently dense for gel loading. The resuspended phage mixture is then loaded onto an SAS-polyacrylamide gel and electrophoresed (Laemmli et al. (1970) supra).

After electrophoresis, the proteins in the SDS-polyacrylamide gel are transferred to nitrocellulose using standard techniques. The nitrocellulose blot is then soaked briefly in 0.2% Ponceau S in 6% acetic acid to visualize protein bands. The pIII band is relatively sharply resolved. Then the stained blot is rinsed in water or PBS to remove the stain. Then Western blotting is carried out essentially as described in McCafferty et al. (1990) Nature 348:552–554 with the use of Cadbury's brand of skim milk powder.

The inventors note that treatment of the phage in 6% acetic acid prior to electrophoresis is crucial for obtaining successful electropherograms and Western blots. With the acid pretreatment, recombinant phage carrying only one copy of an oligopeptide epitope can be successfully detected by Western blotting.

For topological mapping, an oligonucleotide comprising a sequence encoding amino acids 2–6 of endoplasmin as a tandem repeat of two copies, is chemically synthesized, e.g., using automated DNA synthesis (Model 380B, Applied Biosystems, Inc., Foster City, Calif.). After synthesis and purification, the two strands of the oligonucleotide are allowed to self anneal, appropriate linkers are added, and then inserted into randomized linear f1 RF molecules as previously described (U.S. Pat. Nos. 4,528,266 and 4,359,535 which are incorporated by reference herein).

The recombinant f1 DNA molecules are transfected into competent E. coli cells, and plated. Plaques which result from recombinant phage are identified using conventional hybridization techniques.

Phages are also screened with the endoplasmin-specific antibody described above and labelled second antibody. The immunological screening was carried out essentially as described in McCafferty et al. (1990) supra, except that the nitrocellulose containing the "lifted" plaques was first treated with 0.2% Ponceau S in 6% acetic acid for 3–4 minutes, followed by rinsing in water until destained. As before, Cadbury brand of skim milk powder is used. Isogenic E. coli transfected with unmodified f1 were used as a control in the immunological screen. Recombinant f1 expressing the endoplasmi epitope comprising the pentapeptide sequence are identified by the screen.

For best results when using the BamHI site within the pIII gene for epitope analysis, one should use either a tandem repeat of at least two copies of each pentapeptide sequence encoded, or a single copy of a random pentapeptide target sequence should be flanked with a short oligopeptide sequence, e.g., about three amino acids on either side. This extra peptide sequence associated with the target sequence improves the accessibility of the epitope to antibody for binding. Similarly, the Ponceau S-acetic acid pretreatment of proteins to be blotted allows one to detect epitopes whose coding oligonucleotides are incorporated at the BamHI site within the gene encoding pIII of f1. In topological mapping or in immunological screening of plaque lifts on nitrocellulose, the acid treatment is also key to successful results.

Other Embodiments

Other embodiments are also within the scope of the appended claims.

For example, it is not necessary that the matrix be constructed by immobilizing the antibodies or the amino acid sequences on a substrate. Each hybridoma producing an antibody can be cultured separately, and each recombinant virus or modified host cell producing a peptide sequence can be cultured separately. Each antibody is tested individually with each peptide sequence. Correspondence between individual antibodies and the peptide sequences recognized by them can be recorded. A test species can then be tested against each of the individual antibody producing cultures. Any antibodies that bind to the test species can be identified, and the specific peptide sequence recognized by the antibody can be determined by the corresponding peptide sequence-producing culture. Similarly, a test antibody can be tested against each of the individual peptide sequence producing cultures. The specific peptide sequence or sequences recognized by the test antibody can be determined directly by characterizing the unique peptide sequence produced by any cultures that show a positive binding response with the test antibody. This general method can readily be applied to any of the specific uses of a matrix set forth above.

In a further alternative embodiment of the invention, a submatrix can be created containing those antibody-peptide sequence binding pairs that are reactive with a test species of interest. The test species can be a peptide, enzyme, protein, a non-peptide drug, or other non-peptide bioactive substance. The test species is screened on a matrix containing a full range of antibodies and peptide sequences. Those antibody-peptide sequence binding pairs reactive with the test species are selected to form a submatrix. The submatrix is useful in further investigation of the immunological and conformational properties of the test species.

The skilled artisan will understand that any of the aforementioned vectors may be substituted or that other vectors known in the art may be used, providing sequences can be inserted in frame and that expressed random epitopes are expressed in such a way that they are accessible for antibody screening.

I claim:

1. A population of recombinant vectors comprising:
   a population of filamentous bacteriophage wherein each filamentous bacteriophage comprises a recombinant structural gene wherein each structural gene comprises an insert consisting of one member of an oligonucleotide population and wherein the population of filamentous bacteriophage comprise a plurality of different members of the oligonucleotide population,
   said oligonucleotide population comprising oligonucleotides comprising a coding region consisting of a length from about 4 to about 12 nucleotide triplets, said oligonucleotide population encoding a plurality of corresponding random peptide sequences from about 4 to about 12 L-amino acid residues, and
   wherein said recombinant structural genes are expressed upon transfer of said recombinant vectors into *Escherichia coli* host cells, and wherein expression of the recombinant structural genes yields polypeptides, each poly peptide comprising one of said plurality of corresponding random peptide sequences.

2. The vector population of claim 1 wherein each of the encoded corresponding peptides forms a binding pair with an antibody that has not been elicited by immunization with said peptide or said peptide in conjugated form, said antibody being selected from the group consisting of all antibodies produced by lymphoid-derived antibody-producing cells, where the group of all antibodies together recognizes substantially all epitopic sequences.

3. The recombinant vector population of claim 1, wherein each of said members of said oligonucleotide population has a length of from about 4 to 7 nucleotide triplets and the encoded corresponding peptide sequences have a length of from 4 to 7 L-amino acid residues.

4. The recombinant vector population of claim 1, wherein each of said members of said oligonucleotide population has a coding region having a length of 4 nucleotide triplets and the encoded corresponding peptide sequence has a length of 4 amino acid residues.

5. The recombinant vector population of claim 1, wherein each of said members of said oligonucleotide population has a length of 5 nucleotide triplets and the encoded corresponding peptide sequences have a length of 5 L-amino acid residues.

6. The recombinant vector population of claim 1, wherein each of said members of said oligonucleotide population has a coding region having a length of 6 nucleotide triplets and the encoded corresponding peptide sequence has a length of 6 amino acid residues.

7. The recombinant vector population of claim 1, wherein each of said members of said oligonucleotide population has a coding region having a length of 7 nucleotide triplets and the encoded corresponding peptide sequence has a length of 7 amino acid residues.

8. The recombinant vector population of claim 1, wherein each of said members of said oligonucleotide population has a coding region having a length of 8 nucleotide triplets and the encoded corresponding peptide sequence has a length of 8 amino acid residues.

9. The recombinant vector population of claim 1, wherein each of said members of said oligonucleotide population has a coding region having a length of 9 nucleotide triplets and the encoded corresponding peptide sequence has a length of 9 amino acid residues.

10. The recombinant vector population of claim 1, wherein each of said members of said oligonucleotide population has a coding region having a length of 10 nucleotide triplets and the encoded corresponding peptide sequence has a length of 10 amino acid residues.

11. The recombinant vector population of claim 1, wherein each of said members of said oligonucleotide population has a coding region having a length of 11 nucleotide triplets and the encoded corresponding peptide sequence has a length of 11 amino acid residues.

12. The recombinant vector population of claim 1, wherein each of said members of said oligonucleotide population has a coding region having a length of 12 nucleotide triplets and the encoded corresponding peptide sequence has a length of 12 amino acid residues.

13. The recombinant vector population of claim 1 wherein said filamentous bacteriophage are f1.

14. The recombinant vector population of claim 1 wherein said filamentous bacteriophage are fd.

15. The recombinant vector population of claim 1 wherein said filamentous bacteriophage are M13.

16. The recombinant vector population of claim 1 wherein the sum of corresponding peptide sequences encoded by said oligonucleotide population represents at least about 10% of all possible peptide sequences of said length.

17. The recombinant vector population of claim 1 wherein the sum of the corresponding peptide sequences encoded by said oligonucleotide population includes substantially all possible peptide sequences of said length.

18. A method of producing a population of epitopic peptide sequences, comprising:
   Providing a population of recombinant *Escherichia coli* cells, each of said cells containing at least one member of a recombinant vector population, each member of said vector population comprising filamentous bacteriophage, wherein each filamentous bacteriophage comprises a recombinant structural gene wherein each structural gene comprises an insert consisting of one member of an oligonucleotide population and wherein the population of filamentous bacteriophage comprise a plurality of different members of the oligonucleotide population, said oligonucleotide population comprising oligonucleotides comprising a coding region consisting of a length from about 4 to about 12 nucleotides triplets, said oligonucleotide population encoding a plurality of epitopic peptides consisting of random sequences of from about 4 to about 12 L-amino acid residues: and
   Culturing said recombinant *Escherichia coli* cells to allow expression of said recombinant structural genes such that said epitopic peptide sequences are accessible to antibody recognition.

19. The method of claim 18 wherein the sum of said corresponding epitopic peptide sequences represents substantially all possible peptide sequences of said length.

20. The method of claim 18 wherein the sum of said corresponding epitopic peptide sequences represents at least about 10% of all possible peptide sequences of said length.

21. The method of claim 20 wherein said oligonucleotide population encodes a number of peptide sequences of said length having sufficient conformational similarity with an antibody binding site of a test species such that an antibody that binds to the antibody binding site of the test species also binds a peptide of the encoded plurality of peptides.

22. A population of recombinant vectors comprising substantially identical autonomously replicating nucleic acid sequences comprising a recombinant structural gene, each structural gene having inserted therein a member of an oligonucleotide population, wherein each member of said oligonucleotide population comprises a coding region comprising a length from about 4 to about 12 nucleotide triplets that encodes a corresponding peptide sequence of from about 4 to about 12 L-amino acid residues, and wherein the sum of corresponding peptide sequences encoded by said oligonucleotide population represents at least about 10% of all possible peptide sequences of said length, and wherein each member of said oligonucleotide population is contained in said recombinant vector population, and wherein the recombinant structural genes are expressed upon transfer of said recombinant vectors into *Escherichia coli* host cells, and wherein expression of said recombinant structural genes yields polypeptides, each polypeptide comprising said corresponding peptide sequence.

23. A method of producing a population of epitopic peptide sequences, comprising the steps of:

Providing a population of recombinant *E. coli* cells, each of said cells containing at least one member of a recombinant vector population, each member of said vector population comprising substantially identical autonomously replicating nucleic acid sequences, said nucleic acid sequences comprising a recombinant structural gene, each structural gene having inserted therein a member of an oligonucleotide population wherein each member of said oligonucleotide population comprises a coding region comprising a length from about 4 to about 12 nucleotide triplets that encodes a corresponding peptide sequence of from about 4 to about 12 L-amino acid residues, and wherein each member of said oligonucleotide population is contained in said recombinant vector population and wherein the sum of said corresponding epitopic peptide sequences represents at least about 10% of all possible peptide sequences of said length: and culturing said recombinant *E. coli* cells to allow expression of said recombinant structural genes such that said epitopic peptide sequences are accessible to antibody recognition.

* * * * *